US00PP35820P2

(12) United States Plant Patent
Miyazaki et al.

(10) Patent No.: US PP35,820 P2
(45) Date of Patent: May 21, 2024

(54) ***CALIBRACHOA* PLANT NAMED 'SUNCAL 1231'**

(50) Latin Name: ***Calibrachoa* sp.**
Varietal Denomination: Suncal 1231

(71) Applicants: Kiyoshi Miyazaki, Shiga (JP); Masahiro Yamada, Shiga (JP)

(72) Inventors: Kiyoshi Miyazaki, Shiga (JP); Masahiro Yamada, Shiga (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 18/126,373

(22) Filed: Mar. 24, 2023

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413
CPC . A01H 5/02; A01H 5/00; A01H 6/821; A01H 6/82
See application file for complete search history.

(56) References Cited

PUBLICATIONS

Growerstalk Mar. 31, 2022 Welcome to #Cast2022 Day 2!, retrieved online at https://www.growertalks.com/Newsletters/View/Newsletter/?article=3778, 18 pp. (Year: 2022).*
Suntory Flowers 2024 Catalog, retrieved online at https://suntoryflowers.com/wp-content/uploads/2023/03/2024-Suntory-Flowers-Catalog.pdf, pp. 1-2,46,62. (Year: 2023).*

* cited by examiner

*Primary Examiner* — June Hwu
(74) *Attorney, Agent, or Firm* — C. Anne Whealy

(57) ABSTRACT

A new and distinct cultivar of *Calibrachoa* plant named 'Suncal 1231', characterized by its upright to outwardly spreading and mounding plant habit; vigorous growth habit; freely branching habit; freely flowering habit; long flowering period; reddish orange-colored flowers; and good garden performance.

2 Drawing Sheets

Figure 1:
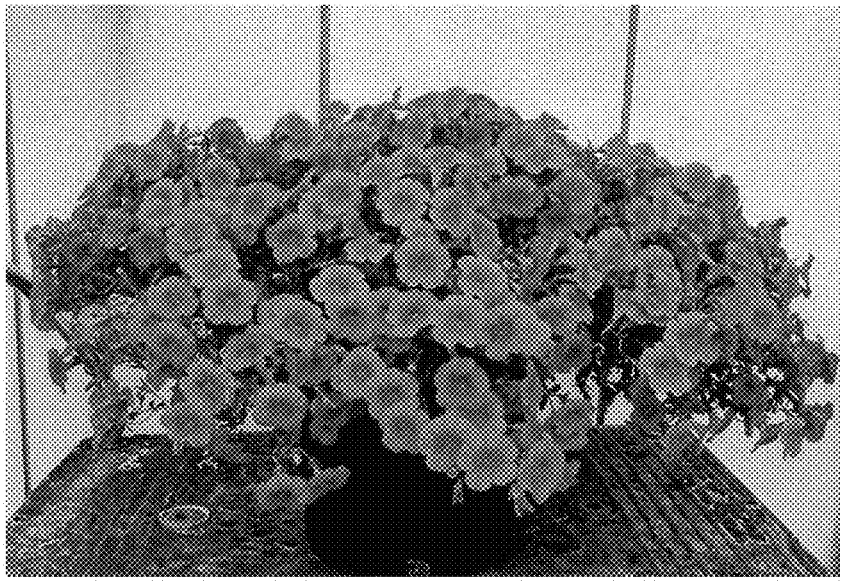

Botanical designation: *Calibrachoa* sp.
Cultivar denomination: 'SUNCAL 1231'.

BACKGROUND OF THE INVENTION

The present invention relates to a new and distinct cultivar of *Calibrachoa* plant, botanically known as *Calibrachoa* sp. and hereinafter referred to by the name 'Suncal 1231'.

The new *Calibrachoa* plant is a product of a planned breeding program conducted by the Inventors in Higashiomi, Shiga, Japan. The objective of the breeding program is to develop new mounding and freely branching *Calibrachoa* plants with numerous large and attractive flowers with unique coloration.

The new *Calibrachoa* plant originated from a cross-pollination conducted by the Inventors in Higashiomi, Shiga, Japan in September, 2013 of a proprietary selection of *Calibrachoa* sp. identified as code number C80, not patented, as the female, or seed, parent with a proprietary selection of *Calibrachoa* sp. identified as code number C65, not patented, as the male, or pollen, parent. The new *Calibrachoa* plant was discovered and selected by the Inventors as a single flowering plant from within the progeny of the stated cross-pollination in a controlled greenhouse environment in Higashiomi, Shiga, Japan in October, 2014.

Asexual reproduction of the new *Calibrachoa* plant by terminal vegetative cuttings in a controlled greenhouse environment in Higashiomi, Shiga, Japan since March, 2016 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Suncal 1231'. These characteristics in combination distinguish 'Suncal 1231' as a new and distinct *Calibrachoa* plant:

1. Upright to outwardly spreading and mounding plant habit.
2. Vigorous growth habit.
3. Freely branching habit.
4. Freely flowering habit.
5. Long flowering period.
6. Reddish orange-colored flowers.
7. Good garden performance.

Plants of the new *Calibrachoa* can be compared to plants of the female parent selection. Plants of the new *Calibrachoa* differ primarily from plants of the female parent selection in flower color as plants of the female parent selection have darker orange-colored flowers.

Plants of the new *Calibrachoa* can be compared to plants of the male parent selection. Plants of the new *Calibrachoa* differ primarily from plants of the male parent selection in flower center color as flowers of plants of the male parent selection have darker orange-colored flower centers.

Plants of the new *Calibrachoa* can also be compared to plants of *Calibrachoa* sp. 'Suncalore', disclosed in U.S. Plant patent application Ser. No. 12/804,918 (abandoned). In side-by-side comparisons, plants of the new *Calibrachoa* and 'Suncalore' differ primarily in the following characteristics:

1. Plants of the new *Calibrachoa* taller and broader than plants of 'Suncalore'.
2. Plants of the new *Calibrachoa* have smaller leaves than plants of 'Suncalore'.
3. Plants of the new *Calibrachoa* have smaller flowers than plants of 'Suncalore'.
4. Flower centers of plants of the new *Calibrachoa* are lighter reddish orange in color than flower centers of plants of 'Suncalore'.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph on the first sheet (FIG. 1) is a side perspective view of a typical flowering plant of 'Suncal 1231' grown in a container.

Figure 2:
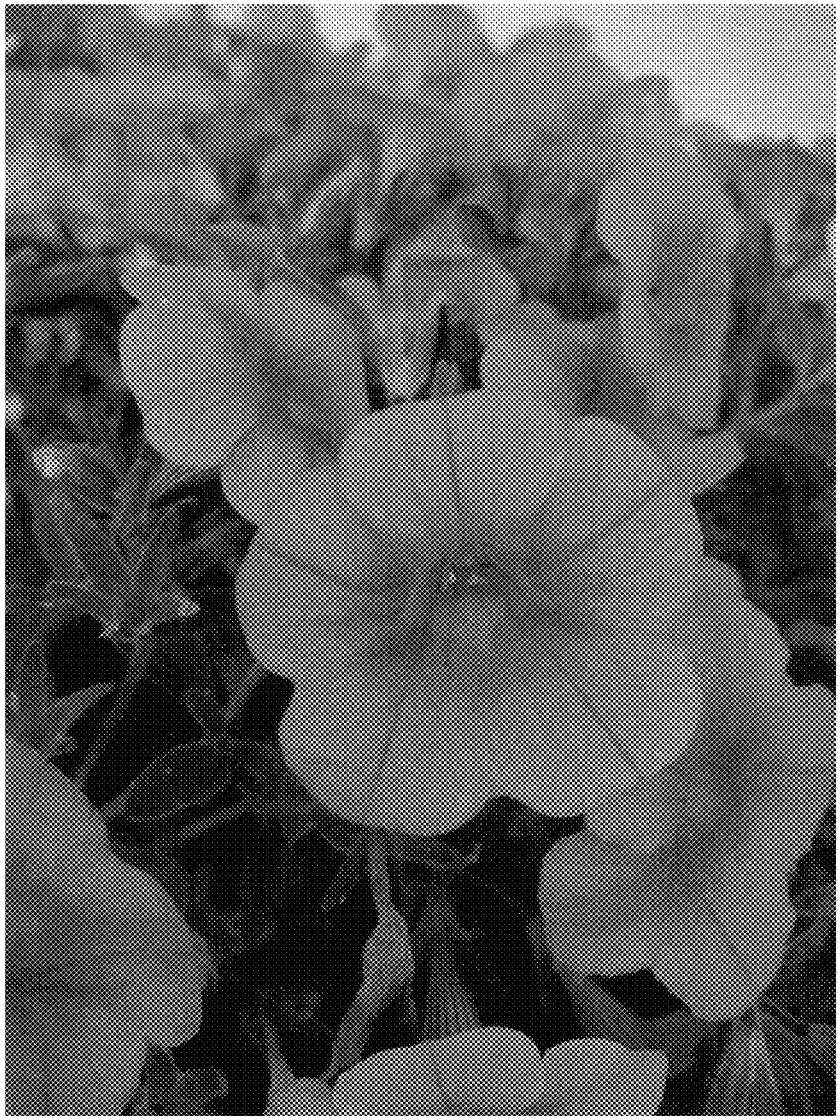

The photograph on the second sheet (FIG. 2) is a close-up view of a typical flowering plant of 'Suncal 1231'.

DETAILED BOTANICAL DESCRIPTION

The aforementioned photographs and following observations, measurements and values describe plants grown during the summer in 24-cm containers in an outdoor nursery in Higashiomi, Shiga, Japan and under cultural practices typical of commercial *Calibrachoa* production. During the production of the plants, day temperatures averaged 23C and night temperatures averaged 13C. Plants were four months old when the photographs and the description were taken. In the following description, color references are made to The Royal Horticultural Society Colour Chart, 2015 Edition, except where general terms of ordinary dictionary significance are used.

Botanical classification: *Calibrachoa* sp. 'Suncal 1231'.

Parentage:

*Female, or seed, parent.*—Proprietary selection of *Calibrachoa* sp. identified as code number C80, not patented.

*Male, or pollen, parent.*—Proprietary selection of *Calibrachoa* sp. identified as code number C65, not patented.

Propagation:

*Type.*—By vegetative terminal cuttings.

*Time to initiate roots, summer and winter.*—About one week at temperatures about 15C to 20C.

*Time to produce a rooted young plant, summer and winter.*—About three weeks at temperatures about 15C to 20C.

*Root description.*—Fibrous; typically white in color; actual color of the roots is dependent on substrate composition, water quality, fertilizer type and formulation, substrate temperature and physiological age of roots.

*Rooting habit.*—Freely branching; dense.

Plant description:

*Plant and growth habit.*—Upright to outwardly spreading and mounding plant habit; freely branching habit with numerous lateral branches developing per plant; pinching enhances lateral branch development; vigorous growth habit.

*Plant height.*—About 23 cm.

*Plant diameter.*—About 68 cm.

Lateral branch description:

*Length.*—About 25.8 cm.

*Diameter.*—About 1.2 mm.

*Internode length.*—About 1.3 cm.

*Strength.*—Strong.

*Aspect.*—Upright to somewhat outwardly.

*Texture.*—Densely pubescent; rough.

*Color.*—Close to 138B.

Leaf description:

*Arrangement and quantity.*—Alternate, simple; about 20 leaves per lateral branch.

*Length.*—About 2.6 cm.

*Width.*—About 4.9 mm.

*Shape.*—Elliptic.

*Apex.*—Narrowly acute.

*Base.*—Attenuate.

*Margin.*—Entire.

*Texture, upper and lower surfaces.*—Densely pubescent; rough.

*Venation pattern.*—Pinnate; reticulate.

*Color.*—Developing and fully expanded leaves, upper surface: Close to 137B; venation, close to 138B. Developing and fully expanded leaves, lower surface: Close to 137C; venation, close to 138B.

*Petioles.*—Length: About 3.5 mm. Diameter: About 1.8 mm. Texture, upper and lower surfaces: Pubescent; rough. Color, upper and lower surfaces: Close to 138B.

Flower description:

*Flower arrangement and habit.*—Single salverform flowers arising from upper leaf axils; freely flowering habit with usually about 297 flowers developing per plant; flowers face mostly upright to outwardly.

*Fragrance.*—None detected.

*Natural flowering season.*—Early flowering habit, plants of the new *Calibrachoa* initiate and develop flowers about three to four weeks after planting; long flowering period, flowering naturally commences during the spring and plants flower continuously throughout the summer into the late autumn in Japan.

*Flower longevity.*—Individual flowers last about seven to ten days on the plant; flowers not persistent.

*Flower buds.*—Length: About 1.9 cm. Diameter: About 5.2 mm. Shape: Cylindrical. Color: Distally, close to 173B and proximally, close to 151C; venation, close to 152A.

*Flower diameter.*—About 2.9 cm.

*Flower length (depth).*—About 7.9 mm.

*Throat diameter.*—About 7 mm.

*Tube length.*—About 1.6 cm.

*Tube diameter, proximally.*—About 2.1 mm.

*Corolla.*—Arrangement: Five petals fused at the base and opening into a flared trumpet; moderately lobed. Petal length from throat: About 8.8 mm. Petal width: About 10.8 mm. Petal shape: Roughly spatulate. Petal apex: Rounded, blunt. Petal margin: Entire; slightly undulate. Petal texture, upper and lower surfaces: Smooth, glabrous. Throat texture: Smooth, glabrous. Tube texture: Smooth, glabrous. Color: Petal, when opening, upper surface: Close to 33B. Petal, when opening, lower surface: Close to 33C. Petal, fully opened, upper surface: Close to 32B; towards the throat, close to 33B; venation, strongly conspicuous and close to 32A; color does not change with subsequent development. Petal, fully opened, lower surface: Close to 32C; color does not change with subsequent development. Throat: Close to 32A; proximally, close to 17C; venation, close to 152C. Tube: Close to 2A; venation, close to 152D.

*Calyx.*—Arrangement: Star-shaped tubular calyx tube with five sepals in a single whorl and fused at the base. Sepal length: About 7.5 mm. Sepal width: About 2.2 mm. Sepal shape: Lanceolate. Sepal apex: Acute. Sepal margin: Entire. Sepal texture, upper and lower surfaces: Pubescent; rough. Sepal color: Immature and mature, upper surface: Close to 137B. Immature and mature, lower surface: Close to 137C.

*Peduncles.*—Length: About 8.6 mm. Diameter: About 0.8 mm. Angle: Upright to somewhat outwardly. Strength: Strong. Texture: Pubescent; rough. Color: Close to 138B.

*Reproductive organs.*—Stamens: Quantity: Five per flower. Filament length: About 7.1 mm. Filament color: Close to 145D. Anther shape: Ellipsoidal. Anther size: About 1.3 mm by 1.5 mm. Anther color: Close to 8A. Pollen amount: Sparse. Pollen color: Close to 8A. Pistils: Quantity: One per flower. Pistil length: About 1.1 cm. Style color: Close to 145B. Stigma shape: Transversely ellipsoidal. Stigma color: Close to 145B. Ovary color: Close to 145B.

*Seeds and fruits.*—To date, seed and fruit development have not been observed on plants of the new *Calibrachoa.*

Garden performance: Plants of the new *Calibrachoa* have been observed to have good garden performance and to tolerate wind, rain and temperatures ranging from about 5C to about 35C.

Pathogen & pest resistance: To date, plants of the new *Calibrachoa* have not been observed to be resistant to pathogens and pests common to *Calibrachoa* plants.

It is claimed:

1. A new and distinct *Calibrachoa* plant named 'Suncal 1231' as illustrated and described.

* * * * *